US 9,557,905 B2

(12) United States Patent
Sabourin

(10) Patent No.: US 9,557,905 B2
(45) Date of Patent: Jan. 31, 2017

(54) SYSTEM AND METHOD FOR USER INPUT

(71) Applicant: General Electric Company, Schenectady, NY (US)

(72) Inventor: Thomas Sabourin, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 373 days.

(21) Appl. No.: 14/132,869

(22) Filed: Dec. 18, 2013

(65) Prior Publication Data
US 2015/0172536 A1 Jun. 18, 2015

(51) Int. Cl.
*H04N 5/232* (2006.01)
*G06F 3/0484* (2013.01)
*G06F 3/01* (2006.01)
*G06F 3/023* (2006.01)
*G06F 3/03* (2006.01)
*G06F 3/042* (2006.01)
*A61B 8/00* (2006.01)

(52) U.S. Cl.
CPC ........... *G06F 3/04847* (2013.01); *A61B 8/467* (2013.01); *G06F 3/011* (2013.01); *G06F 3/017* (2013.01); *G06F 3/0233* (2013.01); *G06F 3/0304* (2013.01); *G06F 3/0426* (2013.01); *A61B 8/54* (2013.01)

(58) Field of Classification Search
None
See application file for complete search history.

(56) References Cited

U.S. PATENT DOCUMENTS

| 7,340,314 B1* | 3/2008 | Duncan | G06F 21/604 340/506 |
|---|---|---|---|
| 8,228,315 B1 | 7/2012 | Starner et al. | |
| 2005/0004630 A1* | 1/2005 | Kagermeier | A61B 5/0002 607/60 |
| 2008/0297614 A1 | 12/2008 | Lieberman et al. | |
| 2012/0268376 A1 | 10/2012 | Bi | |
| 2013/0225999 A1* | 8/2013 | Banjanin | A61B 8/467 600/443 |
| 2014/0085185 A1* | 3/2014 | Sarwar | G06F 3/017 345/156 |
| 2015/0054761 A1* | 2/2015 | Kim | G06F 3/04886 345/173 |

* cited by examiner

*Primary Examiner* — Sath V Perungavoor
*Assistant Examiner* — Janese Duley

(57) ABSTRACT

A medical diagnostic imaging system comprises a user interface comprising at least one physical control. The system also comprises a camera positioned to view the physical control. The system further comprises a processor connected to the camera and configured to detect a manipulation involving the physical control and associate the manipulation with a desired user input for controlling the imaging system.

18 Claims, 4 Drawing Sheets

SYSTEM AND METHOD FOR USER INPUT

BACKGROUND OF THE INVENTION

The subject matter disclosed herein relates to medical diagnostic imaging systems, such as an ultrasound imaging system, and more particularly to a user input system for such imaging systems.

Cleaning and sterilizing the user interface of a medical diagnostic imaging system, such as an ultrasound system, can be a challenge. The chemicals used to clean and sterilize can hinder the operation of and even damage electronic components and controls. Different approaches have been employed in attempt to solve this problem. For example, tempered glass touch sensitive interfaces have been employed. However, this attempted solution suffers from the disadvantage that an operator, such as an ultrasound sonographer, may find it difficult to control the ultrasound system with one hand while viewing the image on the display as they are scanning the subject with a probe held in the other hand. This is because the operator must often and repeatedly look away from the display to the control panel to change the settings of the system. Having controls that the operator can identify by touch without looking at them may allow the operator to better focus on the images or behavior of the system while simultaneously modifying various settings because there is less need to look at the controls.

Therefore, a system and method of controlling a medical diagnostic imaging system that can be easily sterilized without fear of damage to electrical components and easily operated by an operator without repeatedly looking at the controls is desired.

BRIEF DESCRIPTION OF THE INVENTION

The above-mentioned shortcomings, disadvantages and problems are addressed herein which will be understood by reading and understanding the following specification.

In an embodiment a medical diagnostic imaging system comprises a user interface comprising at least one physical control. The system also comprises a camera positioned to view the physical control. The system further comprises a processor connected to the camera and configured to detect a manipulation involving the physical control and associate the manipulation with a desired user input for controlling the imaging system.

In another embodiment, a method for controlling a medical diagnostic imaging comprises providing a user interface comprising at least one physical control and viewing with a camera the physical control. The method further comprises detecting with a processor a manipulation of the physical control, and associating the manipulation with a desired user input for controlling the imaging system.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
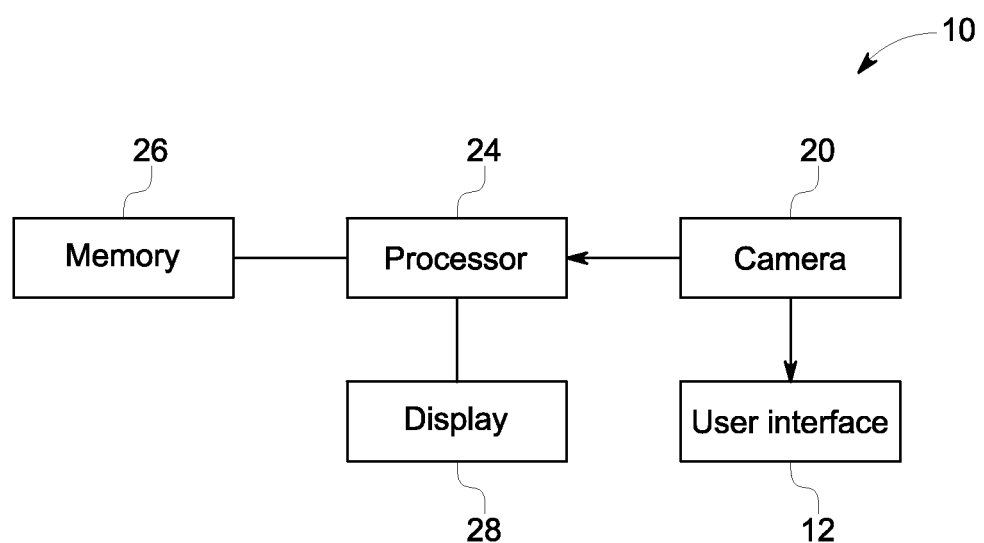
FIG. 1 is a schematic diagram of a medical diagnostic imaging system in accordance with an embodiment of the disclosure.

FIG. 1 is a schematic diagram of a medical diagnostic imaging system 10 in accordance with an embodiment of the disclosure. The medical diagnostic imaging system 10 will hereinafter be described and illustrated as an ultrasound system. It should be appreciated, however, that other types of medical diagnostic imaging systems may be envisioned for implementing various embodiments of the invention. The ultrasound system 10 comprises a user interface 12. The user interface 12 may be used to control the ultrasound system 10.

Figure 2:
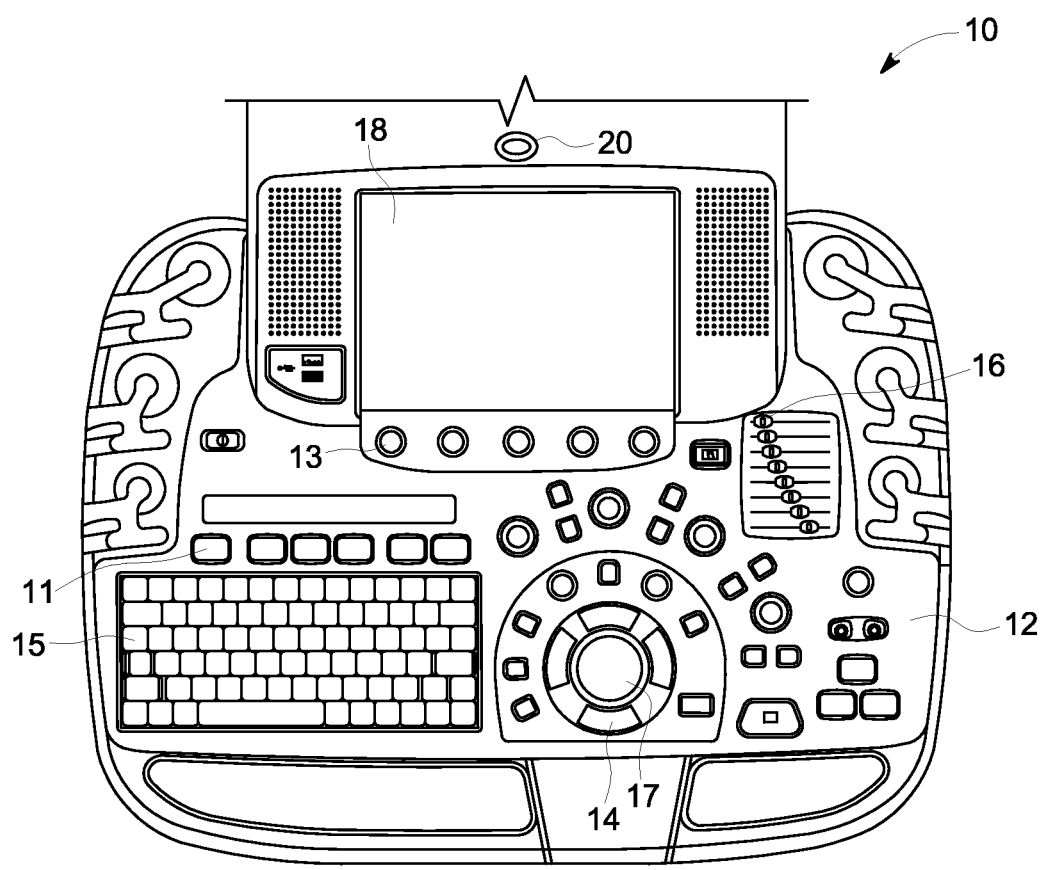
FIG. 2 is a top view of an ultrasound system in accordance with an embodiment of the disclosure.

FIG. 2 is a top view of the ultrasound system 10 in accordance with an embodiment of the disclosure. In the illustrated embodiment, the user interface 12 comprises a plurality of physical controls 11 and 13-17, but may also comprise an electronic control 18, or a combination thereof. It should be appreciated that physical controls identified by reference numerals 11 and 13-17 are exemplary and each may be positioned in various locations within the user interface 12.

The ultrasound system 10 also comprises a camera 20. The camera 20 may be an optical camera or an infrared camera designed to pick up ambient light in the environment. Alternatively, the camera 20 may be designed to detect light (e.g., LED) from a projector positioned to project on the physical controls. The camera 20 may be integrated into the ultrasound system 10, or may be separately attachable to the exterior of the ultrasound system 20 or even mounted to a shelf, wall or another fixture positioned nearby the system 20. The camera 20 may be positioned in proximity to the user interface 12 and configured to view a manipulation involving the physical controls 11 and 13-17. Additionally, it should be appreciated that ultrasound system 10 may comprise more than one camera 20 in order to more robustly view a variety of user manipulations.

The ultrasound system 10 further comprises a processor 24 which is electrically connected to the camera 20, memory 26 and display 28. In this context, the term "electrically connected" (and obvious variants such as "electronic connection") refers to a wired connection for conveying electronic signals (which may be digital or analog) from one device or component to another. In one embodiment, the processor 24 may be electrically connected to at least a portion of user interface 12 when the user interface 12 comprises the electronic control 18. By contrast, the physical controls 11 and 13-17 are not electrically connected to the processor 24 and do not themselves generate electronic signals. Instead, the processor 24 is configured to receive images from the camera 20 and to analyze such images for detecting a manipulation of the physical controls 11 and 13-17. The processor 24 is further configured to associate the manipulation with a desired user input for the ultrasound system 10. The processor 24 may also be configured to control the display 28.

The memory 26 may be a non-transitory computer readable storage medium. Memory 26 is configured to store a reference set of manipulations and at least one mapping between each of those manipulations and associated user inputs for the ultrasound system 10. The memory 26 may contain additional data, instructions or programs.

Display 28 is configured to display and convey information to a user. For example, in one embodiment the display 28 is configured to display an ultrasound image. In another embodiment, the display 28 is configured to convey setting information relating to the ultrasound system 10. For example, a user could replace the user interface 12 with an alternative, modularized, user interface comprising a different arrangement of physical controls that may be mapped to additional manipulations. In yet another embodiment, the display 28 is configured to convey information about a current mapping between the manipulations and desired user inputs as applied by the processor 24 so the user can understand such mapping and optionally modify it.

Each of the physical controls 11 and 13-17 may be movable or immovable. Various embodiments of movable physical controls may be envisioned. In one embodiment, the physical controls 11 and 14 comprise buttons that are configured to be depressed and automatically return to their raised positions once downward pressure from the user ceases or, alternatively, one or both of them may toggle between raised and lowered positions on alternate presses by the user. In another embodiment, the physical control 15 comprises a plurality of depressible buttons or keys that form a keyboard. In another embodiment, the physical control 13 is a rotatable knob that is configured to be rotated about an axis. In another embodiment, the physical control 16 is a slider, configured to be moved back and forth along a line. In yet another embodiment, the physical control 17 is a trackball that is configured to rotate about a point. It should be appreciated, however, that additional embodiments of the physical control 11 may be envisioned.

Manipulation of the movable physical controls may comprise actual movements. For example, the actual movement may comprise sliding, rotating, pushing/pulling, rolling, or a combination thereof. It should be appreciated that other movements may be envisioned. Alternately, the manipulation may comprise a gesture about or in proximity to the movable controls. The gesture may comprise a sliding motion, a rotating motion, a pushing/pulling motion, a rolling motion, or a combination thereof. It should be appreciated, however, that other gestures about or in proximity to the movable physical controls may be envisioned.

One or more of the physical controls 11 and 13-17 may alternatively be immovable. Various embodiments of immovable physical controls are envisioned. For example, the buttons 11 and 14, the knob 13, the keyboard 15, the slider 16, and the trackball 17 may be stationary rather than movable. Since actual movement of an immovable physical control is not possible, the manipulation of the immovable physical control may be a gesture done by the user in the same manner as if the control were movable. The gesture may comprise a sliding motion, a rotating motion, a pushing/pulling motion, a rolling motion, or a combination thereof. It should be appreciated, however, that other gestures about or in proximity to the immovable physical controls may be envisioned.

Optionally, one or more of the physical controls 11 and 13-17 could include indicia to facilitate the processor 24 recognizing the manipulation. For example, the indicia could comprise printed text, a particular color, pattern or a surface texture that is easily recognized by the processor 24.

The user interface 12 may also comprise the electronic control 18. Unlike the physical controls 11 and 13-17, the electronic control 18 is electrically connected to processor 24. Manipulation of the electronic control 18 by a user may generate an electronic input to control the ultrasound system 10. For example, in one embodiment, the electronic control 18 may comprise a touchscreen, wherein the touchscreen comprises a plurality of soft keys configured to receive a user manipulation and generate an electronic signal that is conveyed to the processor 24.

Figure 3:
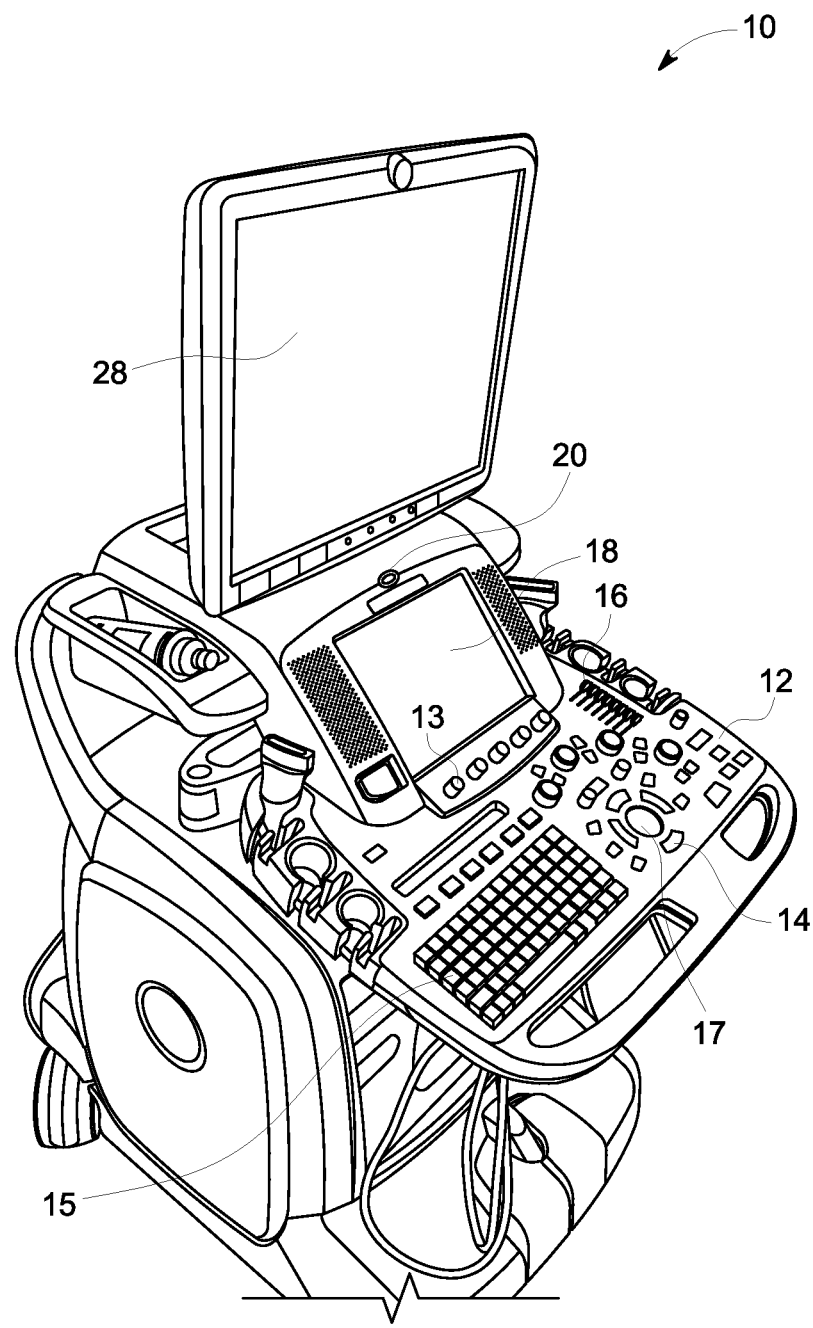
FIG. 3 is a perspective view of an ultrasound system in accordance with an embodiment of the disclosure.

FIG. 3 is a perspective view of the ultrasound system 10 in accordance with an embodiment of the disclosure. As described with respect to FIG. 1, the ultrasound system 10 may comprise user interface 12, camera 20 and display 28. The camera 20 is positioned in proximity to the user interface 12 to view and/or record user interaction with the user interface 12. Specifically, the camera 20 is positioned to view and/or record user manipulation of the physical controls 11 and 13-17. In the depicted embodiment, the camera 20 is positioned vertically above and to the anterior side of the user interface 12. However, it should be appreciated that other positions of the camera 20 with respect to the user interface 12 may be envisioned. For example, the camera 20 may be positioned laterally with respect to the user interface 12.

Figure 4:
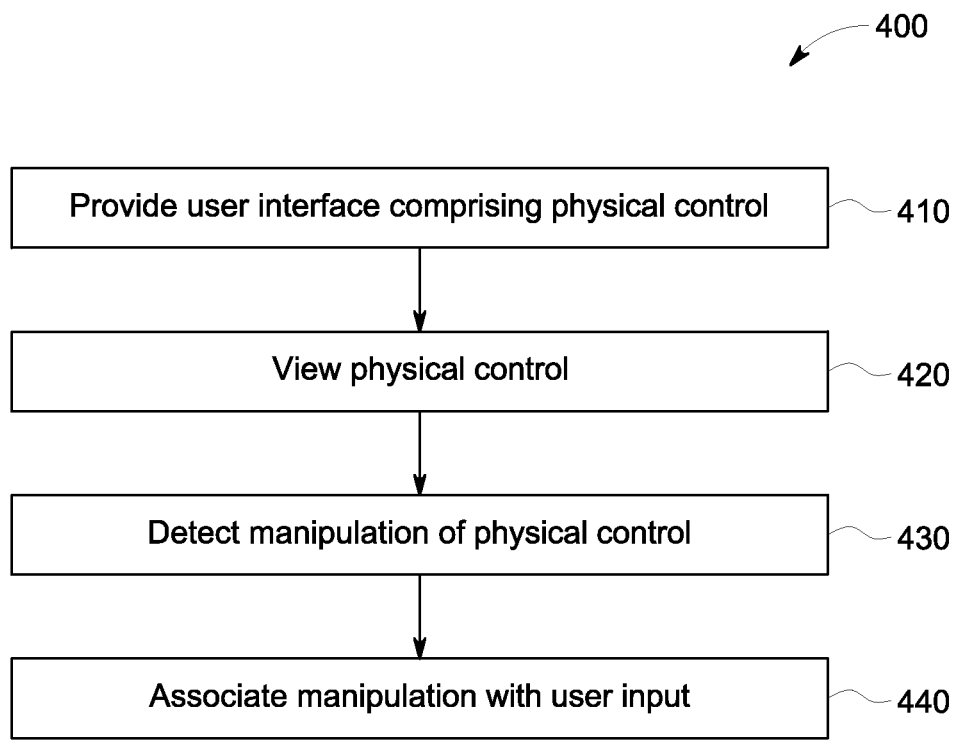
FIG. 4 is a flow diagram illustrating a method for controlling a medical diagnostic imaging system.

Having described the components of the ultrasound system 10, an exemplary method 400 for controlling the medical diagnostic imaging system 10 will now be described in connection with FIG. 4. The method 400 may include a step 410 comprising providing ultrasound system 10 with the user interface 12 including the physical controls 11 and 13-17. As discussed with reference to FIGS. 2 and 3, the physical controls 11 and 13-17 may be movable or immovable. The physical controls 11 and 13-17 may comprise, for example, various combinations of knobs, buttons, keyboards, sliders, trackballs, or similar input devices that are well known to operators of such systems.

The method 400 may also include a step 420 comprising viewing with a camera 20 the physical controls 11 and 13-17. The camera 20 may be positioned in proximity to the user interface 12. For example, the camera 20 may be positioned vertically above and to the anterior side of the user interface 12. In another embodiment, the camera 20 may be positioned to a lateral side of the user interface 12. The camera 20 is configured to view a manipulation of the physical controls 11 and 13-17.

The method 400 may also include a step 430 comprising detecting with the processor 24 a manipulation of the physical controls 11 and 13-17. The processor is electrically connected to camera 20 and is configured to receive images from the camera 20. The manipulation may comprise an actual movement of the physical controls 11 and 13-17 or, alternatively, a gesture by the user related to the physical controls 11 and 13-17. The movement may include sliding, rotating, pushing/pulling, rolling, or a combination thereof. It should be appreciated that other movements may be envisioned. Movement of the physical controls 11 and 13-17 may be detected based on a change of position thereof. The gesture may include a sliding motion, a rotating motion, a pushing/pulling motion, a rolling motion, or a combination thereof. It should be appreciated, however, that other gestures about or in proximity to the movable physical controls 11 and 13-17 may be envisioned. In an example, the processor 24 may detect movement of button 14 based on a change of position of an indentation thereon. In another example, the processor 24 may detect rotation of knob 13 based on a change of position of a protrusion thereon. In yet another example, the processor 24 may detect a typing gesture as if keyboard 15 were movable even when it is immovable.

The method 400 may also include a step 440 comprising associating the manipulation with a desired user input for controlling the ultrasound system. The memory 26 is configured to store a reference set of manipulations as well as a current mapping between such manipulations and associated user inputs for controlling the ultrasound system 10. The memory 26 may contain additional data, instructions or programs. For example, an actual depression (or simply a user gesture of depressing) of button 14 may be associated with selecting a portion of on an image on the display 28. In another example, rotating (or simply a user gesture of rotating) knob 13 may be associated with zooming in on a selected image on the display 28.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A medical diagnostic imaging system, comprising:
a memory;
a processor in electronic communication with the memory;
a user interface comprising at least one physical control, wherein the physical control is not configured to be electrically connected to the processor;
a camera in electronic communication with the processor, where the camera is positioned to view the physical control;
wherein the processor is configured to:
receive images from the camera, where the images show a manipulation of the physical control by a user;
analyze the images to detect the manipulation of the physical control;
associate the manipulation of the physical control with a desired user input for controlling the medical diagnostic imaging system based on a mapping stored in the memory.

2. The system of claim 1, wherein the physical control comprises one of a knob, a button, a slider, and a trackball.

3. The system of claim 1, wherein the physical control is movable and the manipulation involves actual movement of the physical control.

4. The system of claim 3, wherein the physical control comprises indicia configured to facilitate detection of the manipulation by the processor.

5. The system of claim 4, wherein the indicia is selected from a text, a color, a pattern, or a surface texture.

6. The system of claim 1, wherein the physical control is immovable and the manipulation involves a gesture as if the physical control were movable.

7. The system of claim 6, wherein the gesture is a sliding motion, a rotating motion, a pushing motion or a rolling motion.

8. The system of claim 1, wherein the association of the manipulation with the desired user input is modifiable.

9. The system of claim 1, wherein the camera is integrated into the system.

10. The system of claim 1, wherein the camera is separately attachable to the exterior of the system.

11. The system of claim 1, wherein the processor is further configured to control the medical diagnostic imaging system based on the desired user input.

12. A method for controlling a medical diagnostic imaging system comprising:
providing a user interface comprising at least one physical control, wherein the physical control is not configured to generate an electronic input signal to the processor;
viewing with a camera the physical control;
receiving images from the camera with a processor, where the images show a manipulation of the physical control by a user;
analyzing the images with the processor to detect the manipulation of the physical control; and
associating, with the processor, the manipulation of the physical control with a desired user input for controlling the medical diagnostic imaging system based on a mapping stored in a memory.

13. The method of claim 12, wherein the physical control comprises one of a knob, a button, a slider, and a trackball.

14. The method of claim 12, wherein the physical control is movable and the manipulation involves actual movement of the physical control.

15. The method of claim 14, wherein the physical control comprises indicia configured to facilitate detection of the manipulation by the processor.

16. The method of claim 12, wherein the physical control is immovable and the manipulation involves a gesture as if the physical control were movable.

17. The method of claim 16, wherein the gesture is a sliding motion, a rotating motion, a pushing motion or a rolling motion.

18. The method of claim 12, further comprising controlling, with the processor, the ultrasound system based on the desired user input.

* * * * *